United States Patent [19]

Kodama et al.

[11] 3,975,533

[45] Aug. 17, 1976

[54] THERAPEUTIC AGENTS

[75] Inventors: Jiro K. Kodama, Herne Bay, England; George R. Haynes; James R. Albert, both of Modesto, Calif.

[73] Assignee: Shell Oil Company, Houston, Tex.

[22] Filed: Jan. 10, 1972

[21] Appl. No.: 216,775

Related U.S. Application Data

[60] Division of Ser. No. 33,058, April 29, 1970, Pat. No. 3,658,993, which is a continuation-in-part of Ser. No. 674,753, Oct. 12, 1967, abandoned.

[52] U.S. Cl. .............................. 424/326; 424/244; 424/251; 424/273
[51] Int. Cl.² ..................................... A61K 31/155
[58] Field of Search ............ 424/326, 251, 244, 273

[56] References Cited
FOREIGN PATENTS OR APPLICATIONS
1,019,120   2/1966   United Kingdom ................ 424/326

OTHER PUBLICATIONS
Chemical Abstracts 54: 2367i (1960).

*Primary Examiner*—Jerome D. Goldberg

[57] ABSTRACT o-halobenzylideneaminoguanidines are employed as central nervous system depressants, as cardiovascular depressants, and/or as antidepressants for overcoming psychic depression.

2 Claims, No Drawings

THERAPEUTIC AGENTS

This application is a division of Ser. No. 33,058 filed Apr. 29, 1970, now U.S. Pat. No. 3,658,993, issued Apr. 25, 1972, which is a continuation in part of Ser. No. 674,753, filed Oct. 12, 1967, now abandoned.

BACKGROUND OF THE INVENTION

Description of the Prior Art

German Pat. No. 958,832 describes certain benzylideneaminoguanidines and their use as pharmaceuticals and therapeutic agents. Among these guanidines are those in which halogen is substituted on the phenyl ring, specifically, the aminoguanidines which can be considered to be the derivatives of 4-chlorobenzaldehyde, 3,4-dichlorobenzaldehyde and 3-chlorobenzaldehyde. Generically, the patent also discloses the aminoguanidines wich can be considered to be the derivatives of the corresponding halo-acetophenones.

SUMMARY OF THE INVENTION

Despite the teachings of the German patent, it has been found that the aminoguanidines disclosed therein — which do not have halogen substituted at an ortho position on the phenyl ring — exhibit little, if any, pharmacological activity.

In contrast, it has been found that benzylideneaminoguanidines having halogen substituted on at least one of the ortho carbon atoms of the phenyl ring exhibit very high pharmacological activity, particularly acting as depressants of the central nervous system and the cardiovascular system, and as anti-depressants for overcoming psychic depression.

DESCRIPTION OF THE PREFERRED EMBODIMENTS

The pharmacologically active aminoguanidines of the invention can be described by the formula:

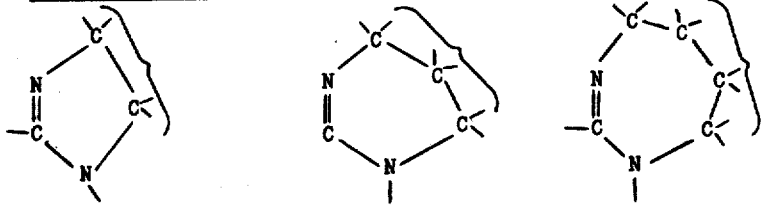

wherein X is halogen or trifluoromethyl, Y and Z may be the same or different and are hydrogen, halogen, trifluoromethyl or $C_1$–$C_4$ alkyl, R, R', R'' and R° each is hydrogen, $C_1$–$C_4$ alkyl, $C_2$–$C_4$ alkenyl or $C_2$–$C_4$ alkynyl, with the proviso that R'' and R° may together form an alkylene or alkenylene bridge of 2 to 4 carbon atoms, and with the further proviso that one of Y and R must be hydrogen. The term "alkylene or alkenylene bridge of 2 to 4 carbon atoms" is illustrated in the following examples, as indicated by the brackets:

alkylene bridge

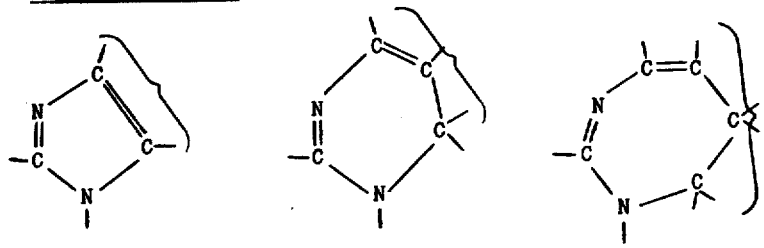

alkenylene bridge

Also suitable are the physiologically acceptable salts of these guanidines, including their salts with such acids as hydrochloric acid, hydriodic acid, acetic acid, sulfuric acid, phosphoric acid, malic acid ethionic acid, malonic acid, citric acid, benzoic acid, and pamoic acid.

In these compounds, X preferably is middle halogen — that is, chlorine or bromine — Y is middle halogen, Z is hydrogen or middle halogen, and R, R', R'' and R° are all hydrogen. Of the salts, the hydrochloride salts are preferred.

Typical, illustrative species of this class of pharmaceuticals are set out in the working examples, as well as the following:

1-(2-chloro-6-(trifluoromethyl)benzylideneamino)-guanidine
1-(2-chloro-3,6-bis(trifluoromethyl)benzylideneamino)guanidine
1-(2-chloro-6-bromobenzylideneamino)guanidine
1-(2-6-dibromobenzylideneamino)guanidine
1-(2-bromo-6-methylbenzylideneamino)guanidine
1-(2,3,6-tribromobenzylideneamino)guanidine
1-(2-chloro-6-propylbenzylideneamino)guanidine
1-(2,4,6-trichlorobenzylideneamino)guanidine 1-(2,6-dichloro-4-methylbenzylideneamino)guanidine 1-(2-bromo-6-fluorobenzylideneamino)guanidine 1-(2,6-dichlorobenzylideneamino)-2-propynylguanidine 1-(2,6-dichlorobenzylideneamino)-1,2,3-trimethylguanidine 1-(2,6-dichlorobenzylideneamino)-2,3-vinyleneguanidine 1-(2,6-dibromo-4-methylbenzylideneamino)guanidine 1-(2-chloro-alpha-methylbenzylideneamino)guanidine hydrochloride 1-(2-(trifluoromethyl)-alpha-methylbenzylideneamino)guanidine hydrochloride 1-(2-chlorobenzylideneamino)guanidine hydrochloride 1(2,4-dichloro-alpha-methylbenzylideneamino)-guanidine hydrochloride The aminoguanidines of this invention are suitably administered orally, parenterally, intraperitoneally or intravenously. The compounds are generally crystalline solids and many are slightly to sparingly soluble in most common organic solvents. Some are quite soluble in common pharmaceutical vehicles, including water. As would be expected, the salts are more soluble in water than are the aminoguanidines per se. Using suitable vehicles and techniques of formulation wholly conventional to one skilled in the art, these compounds can be formulated for use as appropriate to the intended mode of administration.

Compositions according to the present invention are comprised of an aminoguanidine of this invention and an acceptable pharmaceutical carrier which may either be solid material or a liquid. Preparations for oral administration can be liquids or solids or any combination of these forms, such as syrups, elixirs, powders, capsules, or tablets. Preparations for administration of the active agent in unit dose form can be powders, compressed tablets, or a powder enclosed in a suitable capsule of absorbable material such as gelatin. The powders or compressed tablets may also comprise suitable excipients and/or diluents such as starch, lactose, stearic acid, magnesium stearate, dextrin or polyvinylpyrrolidone.

Preparations for parenteral or intraperitoneal administration may be sterile solutions or suspensions in liquids such as water, physiological saline, benzyl alcohol, ethyl oleate, methylcellulose, dimethyl sulfoxide polyethylene glycol or other liquid excipients known in the pharmaceutical and veterinary formulation art.

Any of the above preparations may contain the aminoguanidines of the invention as the only active agent or may contain in addition other pharmaceutically active agents.

The unit dosage or therapeutically effective quantity of the aminoguanidines used according to this invention as central nervous system (CNS) depressants and-/or antidepressant agents can vary over fairly wide limits. For oral, intraperitoneal or parenteral administration in some cases, as little as 0.1 milligram of the active material per kilogram of body weight can be effective in obtaining desired antidepressant or CNS depressant response, while seldom will a dosage in excess of about 10 milligrams per kilogram of body weight be required. In general the effective dosage will be of the order of from about 0.1 to 5 milligrams on the same basis. The therapeutically effective quantity used according to this invention as a cardiovascular agent administered, for example, by oral or intravenous means can be, in some cases, as little as 0.01 milligrams of active material per kilogram of body weight to obtain the desired cardiovascular response. Seldom will a dosage in excess of about 10 milligrams (mg) active material per kilogram (kg) of body weight be required. Generally the effective dosage will be of the order of from about 0.01 to 5 mg/kg.

Each dosage unit form — each capsule, tablet, ampoule, or prescribed dose — can contain from about 0.01 percent to about 95 percent of active material, based upon the total. The preferable amount will depend on how the compound is administered and the carrier used. For example, if administered orally as a solid formulation with lactose or cornstarch the formulation will preferably contain about 1 percent to 50 percent by weight of the active material. If administered as a liquid intraperitoneally, parenterally or intravenously, solubility of the compound will be a determining factor and the preferred formulation will contain 0.1 percent to 25 percent by weight or more of the active material. Of course, it is possible to administer the therapeutics without the use of a pharmaceutical carrier.

The therapeutic agents used according to the invention can be administered either prior to or after the onset of the condition to be treated, such as when they are used as a central system depressant to reduce hyperexcitability and induce sedation.

PREPARATION

Methods for preparing these aminoguanidines and their salts are shown in German Pat. No. 958,832. Preparation of particular, illustrative, species of the compounds of this invention is described in the following examples, wherein "parts" means parts by weight, with parts by volume bearing the same relationship to parts by weight as does the liter to the kilogram. In each example, the product is designated by a capital letter, to permit easy, but precise, identification in a later example.

EXAMPLE I

Preparation of
1-(2,6-dichlorobenzylideneamino)guanidine hydrochloride (A)

93 parts of 2,6-dichlorobenzaldehyde, 78 parts of aminoguanidine bicarbonate, 50 parts by volume of concentrated hydrochloric acid and 250 parts by volume of n-butanol were mixed and heated slowly to reflux (120°C). The by-product water was removed azeotropically over a period of 4 hours. The mixture was cooled and filtered to give 105 parts of a white solid melting at 223°–224°C (uncorr.). The identity of the product was confirmed by elemental analysis.

Analysis (percent by weight): Calculated: Cl — 39.8; Cl$^-$ — 13.3; N — 20.9. Found: Cl — 39.3; Cl$^-$ — 13.0; N — 20.6.

EXAMPLE II

Preparation of
1-(2,6-dichlorobenzylideneamino)guanidine (B)

To 40 parts of the hydrochloride salt obtained in Example I in 600 parts by volume of water was added 130 parts by volume of 10% aqueous sodium hydroxide solution. The voluminous precipitate which formed was filtered and washed with water and acetone. Recrystallization from acetonitrile gave 23 parts of a white solid which decomposes at 227°–229°C (uncorr.). The product was identified as 1-(2,6-dichlorobenzylideneamino)guanidine by elemental and infrared spectrum analyses.

Analysis (percent by weight): Calculated: Cl — 30.7; Cl$^-$ — 0. Found: Cl — 30.0, 30.1; Cl$^-$ — <0.1.

EXAMPLE III

Preparation of
1-(2,6-dichlorobenzylideneamino)-2,3-ethyleneguanidine, hydroiodide and hydrochloride a. Hydroiodide salt (C). 12.3 parts of 2,6-dichlorobenzaldehyde and 16 parts of 2-imidazoline-2-ylhydrazine hydroiodide were mixed in 100 parts by volume of absolute ethanol and refluxed at 80°C for 45 minutes. The mixture was cooled and filtered to give 24 parts of a light tan solid which decomposes at 275°–278°C (uncorr.). The product was identified as the hydroiodide salt of 1-(2,6-dichlorobenzylideneamino)-2,3-ethylene guanidine by elemental and infrared spectrum analyses.

Analysis (percent by weight): Calculated Cl — 18.4; I$^-$ 33.0. Found: Cl — 18.8, 19.01; I$^-$ — 33.2, 33.3.

b. Hydrochloride salt (D). To 10 parts of the HI salt from above in 100 parts by volume of water and 150 parts by volume of ethanol was added 50 parts by volume of 10% aqueous sodium hydroxide solution at 40°C. The mixture was cooled to 25°C and filtered. The solid was dissolved in 200 parts by volume of ethanol and treated with 13 parts of gaseous hydrogen chloride. The solvent was removed under water aspirator vacuum at 30°C. The residue was recrystallized from acetonitrile to give 5.6 parts of the hydrochloride salt melting at 232°–233.5°C (uncorr.) identified by elemental and infrared spectrum analyses.

Analysis (percent by weight): Calculated: Cl$^-$ 12.1. Found: Cl$^-$ 12.0.

EXAMPLE IV

Preparation of
1-(alpha-methyl-2-chlorobenzylideneamino)guanidine hydrochloride (P)

8.8 parts of aminoguanidine carbonate, 20 parts of volume of concentrated hydrochloric acid and 150 parts by volume of n-butanol were refluxed to remove the formed water azeotropically. To the resultant solution, 10 parts of 2'-chloroacetophenone was added and refluxing continued for 16 hours.

The solution was concentrated under water aspirator vacuum to give 18.7 parts of a viscous orange liquid which by repeated crystallization gave 4.6 parts of a pink solid melting at 167°–174°C identified by elemental analysis as 1(alpha-methyl-2-chlorobenzylideneamino)guanidine hydrochloride.

Analysis (percent by weight): Calculated: N — 22.7; Cl — 28.8; Cl$^-$ 14.4. Found: N — 22.5; Cl — 28.4; Cl$^-$ — 14.3.

EXAMPLE V

Preparation of other (benzylideneamino)guanidines and salts thereof

The following other benzylideneamino guanidines and/or salts have been prepared from the appropriate aldehydes and guanidines according to the techniques demonstrated in Examples I–II. The table indicates the melting point of the product and comparison of the results of elemental analyses with the calculated values.

Compound

|  |  |  |  |  |  |  | Analysis (Percent by Weight) | |
|---|---|---|---|---|---|---|---|---|
| Y | Z | R | R' | R'' | Salt | Melting Point (°C) | Calculated | Found |
| (E) Cl | H | H | CH$_3$— | H | — | 166.5–167.5 | N - 22.9 | N - 22.3 |
|  |  |  |  |  |  |  | Cl - 29.0 | Cl - 28.7 |
| (F) Cl | H | H | CH$_3$— | H | HCl | 207–208 | Cl$^-$ - 12.6 | Cl$^-$ - 12.4 |
| (G) Cl | H | H | CH$_2$=CHCH$_2$ | H | HI | 98–100 | N - 14.0 | N - 13.4 |
|  |  |  |  |  |  |  | Cl - 17.8 | Cl - 17.8 |
|  |  |  |  |  |  |  | I$^-$ - 31.8 | I$^-$ - 30.5 |
| (H) Cl | H | H | CH$_3$— | CH$_3$— | HI | 211.5–214.5 | Cl - 18.3 | Cl - 17.5 |
|  |  |  |  |  |  |  | N - 14.5 | N - 14.2 |
|  |  |  |  |  |  |  | I$^-$ - 32.8 | I$^-$ - 32.6 |
| (I) Cl | H | H | CH$_3$— | i-C$_3$H$_7$— | HI | 178–179 | N - 13.5 | N - 13.2 |
|  |  |  |  |  |  |  | Cl - 17.1 | Cl - 17.4 |
|  |  |  |  |  |  |  | I$^-$ - 30.6 | I$^-$ - 30.2 |
| (J) Cl | H | H | CH$_3$— | i-C$_3$H$_7$— | HCl | 172–173.5 | Cl - 32.9 | Cl - 32.5 |
|  |  |  |  |  |  |  | Cl$^-$ - 11.0 | Cl$^-$ - 10.7 |
| (K) Cl | H | CH$_3$— | H | H | HCl | 248–249 (Dec) | Cl - 37.8 | Cl - 36.5 |
|  |  |  |  |  |  |  | Cl$^-$ - 12.6 | Cl$^-$ - 12.2 |
| (L) F | H | H | H | H | HCl | 208–209 | Cl - 28.3 | Cl - 27.6 |
|  |  |  |  |  |  |  | Cl$^-$ - 14.1 | Cl$^-$ - 13.7 |
| (M) CH$_3$— | H | H | H | H | HCl | 176–177 | N - 22.7 | N - 22.4 |
|  |  |  |  |  |  |  | Cl - 28.4 | Cl - 28.2 |
|  |  |  |  |  |  |  | Cl$^-$ - 14.4 | Cl$^-$ - 14.7 |
| (N) Cl | 3-Cl | H | H | H | — | 210–211 | N - 21.1 | N - 21.1 |
|  |  |  |  |  |  |  | Cl - 40.2 | Cl - 40.2 |
| (O) Cl | 3-Cl | H | H | H | HCl | 201.5–203 | Cl - 47.0 | Cl - 46.5 |
|  |  |  |  |  |  |  | Cl$^-$ - 11.8 | Cl$^-$ - 11.7 |

Effectiveness

The following examples show the effectiveness of the drugs as used in the various tests as explained in each instance. While a specific method of administration of the drug may be recited for a specific test, it should be noted that the response elicited may be obtained by the other means of administration as well.

EXAMPLE VI

Effectiveness of the benzylideneaminoguanidines of Examples I to IV as antidepressant agents The antidepressant activity of a compound is shown by the absence of ptosis (defined as an eyelid closure of greater than one-half) after injection of reserpine into a treated animal. Following the reserpine challenge test of Chessin et al., J. Pharmac. Exp. Ther. 119, 453 (1957), groups of five or ten mice are given graded doses of the chemical either orally or parenterally and then challenged with reserpine at 5.0 mg/kg I.p. One hundred and twenty minutes later the mice are assessed for their degree of ptosis. Ptosis of less than 50 percent is judged a positive response. Orally, the activity is assessed at the prophylactic time intervals of 1, 3, 5 and 16 hours. When administered intraperitoneally (I.p), the activity is determined at prophylactic intervals of 1, 2 and 4 hours. The dose required to prevent ptosis in 50 percent of the mice ($ED_{50}$) is calculated for each compound at its time of maximal effectiveness.

Following this procedure, the $ED_{50}$ values for the compounds shown in Examples I to IV are shown below along with the corresponding activity for known reference drugs.

| | Antidepressant Activity I.p. $ED_{50}$ ± S.E. (mg/kg) |
|---|---|
| A | 0.33 ± 0.08 |
| B | 0.12 ± 0.04 |
| C | 2.0 ± 0.5 |
| D | 3.3 ± 0.8 |
| E | 1.3 ± 0.4 |
| F | 2.2 + 0.5 |
| G | 4.3 ± 1.3 |
| H | 2.4 ± 0.8 |
| I | 5.7 ± 2.0 |
| J | 4.2 ± 1.0 |
| K | 7.1 ± 2.3 |
| L | 2.2 ± 0.5 |
| M | 1.0 ± 0.2 |
| N | 1.6 ± 0.6 |
| O | 1.1 ± 0.6 |
| P(1-(2-chloro-alpha-methylbenzyl-ideneamino)guanidine)hydrochloride | 7.2 ± 1.1 |
| Q (1-(alpha-methyl-2-trifluoro-methylbenzylideneamino)quanidine hydrochloride) | 7.6 ± 2.2 |
| Tranylcypromine. $SO_4$ | 1.7 ± 0.4 |
| Iproniazid.$PO_4$ | 42 |
| Imipramine.HCl | 24 ± 11 |

EXAMPLE VII

Effectiveness of benzylideneaminoguanidines as central nervous system (CNS) depressants The presence of significant CNS depressant activity of drugs is demonstrated by the following two tests.

a. Pernicious preening test

Pernicious preening is elicited by painting the rear of the mouse with a pilocohesive dye. A violent, unremitting tearing of the stiff, cohering strands of hair constitutes the pernicious preening behavior. The test procedure involves the intraperitoneal injections of the chemical to groups of 10 male mice (23–37 grams). Thirty minutes later, the pilocohesive dye was applied and the absence or presence of pernicious preening was noted for a 10-minute period. According to Wilfon and his co-workers, Fed. Proc. 19, 21 (1960), both tranquilizers and potent analgesics effectively block this unusual behavior in mice. Inhibitory effects have been elicited by other pharmacologic categories, such as sedatives, anti-convulsants, stimulants, amine oxidase inhibitors, antihistamines, and miscellaneous compounds. With these agents, abolition of pernicious preening was generally accompanied by toxic manifestations.

b. Phenylquinone Writhing Test

The phenylquinone writhing test, as developed by Siegmund and associates (Proc. Soc. Exp. Biol. Med. 97, 729 (1957)), is most useful due to its simplicity, reproducibility, sensitivity and ability to assess a variety of psychotropic drugs. It involves the intraperitoneal injection of phenylquinone (2-phenyl-1,4-benzoquinone) to produce a writhing syndrome in mice. Ten male mice (23–27 grams) are used per dose. The writhing syndrome is characterized by the periodic twisting and turning of the lower half of the body, contractions of the muscles in the pelvic area, and extension of the hindlimbs with elevation of the base of the tail. The ability of the test drug in preventing this syndrome constitutes a positive pharmacological action.

Following these procedures, the effective dosages for the compounds of Table I were obtained. These dosages and those for reference drugs are shown in the following table.

TABLE II

| Compound | Pernicious Preening Test I.p. $ED_{50}$ (mg/kg) | Phenylquinone Writhing Test I.P. $ED_{50}$ (mg/kg) |
|---|---|---|
| A | 0.79 ± 0.14 | 0.12 |
| B | 1.2 ± 0.2 | not tested |
| D | 3.0 ± 0.8 | 3.2 |
| F | 3 | 0.76 ± 0.26 |
| J | 8.0 ± 1.9 | not tested |
| K | not tested | 7.2 ± 1.8 |
| L | 4.6 ± 1.5 | not tested |
| M | 1.4 ± 0.3 | 0.21 ± 0.07 |
| O | 9 | 0.88 ± 0.21 |
| Chloropromazine.HCl | 2.6 | not tested |
| Amitriptyline.HCl | 6.2 ± 1.6 | not tested |
| d-Amphetamine.$SO_4$ | 2.7 ± 0.7 | 2.4 |
| Tranylcypromine.$SO_4$ | 4.9 | 3.2 |
| d-Propoxyphene.HCl | 36 | 17.4 ± 4 |

CNS depressant effects mainly tranquilizing in nature were also noted when A, B, C and E were administered to cats and Rhesus monkeys in dosages as low as 0.30 mg/kg in some cases.

EXAMPLE VIII

Effectiveness of Benzylideneaminoguandinies as a Hypotensive Cardiovascular Agent Generally, a hypotensive cardiovascular agent, when appropriately administered to an animal, will induce a decrease of blood pressure. The hypotensive effect obtained by using such an agent may be caused by several mechanisms involving a decrease in peripheral vascular resistance or a decrease in cardiac output. These effects in turn may be mediated through neurogenic actions and/or direct effects on the heart or peripheral blood vessels.

Procedure: Classical anesthetized cat preparations were used to assess cardiovascular activities of the experimental drug when administered intravenously (i.v.). Basal arterial blood pressure, heart-rate, electrocardiogram, respiratory rate and depth, intralumenal duodenal pressure, rectal temperature and nictitating membrane contraction were evaluated. In addition, the responses to standard doses of neurohumoral agents and nerve stimulation were measured.

Using these parameters, the compounds listed in Table III were proven to possess unusually high cardiovascular activities.

Arterial blood pressure was significantly lowered in cats anesthetized with pentobarbital by the intravenous administration of compounds A, B, D, F, J, R[1-(2-chlorobenzylideneamino)guanidine hydrochloride], and S[1-(2,4-dichloro-alpha-methylbenzylideneamino)guanidine hydrochloride]. The heart rate was slowed in most experiments.

TABLE III

| Compound | Dose (mg/kg, i.v.) | Decrease, mm Hg in Systolic/Diastolic Blood Pressure | Change in Heart Rate From Control (rate/min) |
|---|---|---|---|
| A | 0.32 | 25/35 | − 45 |
| B | 0.10 | 65/65 | + 10 |
| D | 1.00 | 30/25 | − 40 |
| F | 3.20 | 20/25 | − 40 |
| J | 1.00 | 20/25 | − 10 |
| R | 0.35 | 25/15 | − 45 |
| S | 1.00 | 10/15 | − 10 |

Formulations

The following examples indicate effective formulations which were prepared using various suitable pharmaceutical carriers.

EXAMPLE IX

Oral formulations

A suitably effective liquid oral formulation of 1-(2,6-dichlorobenzylideneamino)guanidine hydrochloride (compound A) was prepared by dissolving 32 milligrams (mg) of the compound in 10 milliliters (ml) of distilled water. This is approximately a 0.3% by weight (w) solution of the active compound.

An effective solid formulation was prepared by mixing 5 parts by weight of compound A with 95 parts by weight lactose. A solid formulation utilizing cornstarch instead of lactose was also prepared.

EXAMPLE X

Intravenous formulations

An intravenous formulation of compound A was prepared by dissolving 32 mg of the compound in 10 ml of physiological saline solution.

EXAMPLE XI

Parenteral or intraperitoneal formulations

Formulations suitable for parenteral (P) or intraperitoneal (I.p) administration were prepared in several ways. For example: (1) 32 mg of compound A were dissolved in 10 ml of distilled water; (2) 32 mg of compound A were dissolved in 10 ml of a 0.5%w solution of methylcellulose in distilled water; (3) 32 mg of compound A were dissolved in a mixture of 1.0 ml polyethylene glycol 400 and 9.0 ml of a 0.5%w methylcellulose solution in distilled water.

A formulation suitable for P or I.p. administration of 1-(2,6-dichlorobenzylideneamino)guanidine, per se, was prepared by mixing 32 mg of this compound with 9.0 ml of a 0.5% methylcellulose solution in distilled water and 1.0 ml polyethylene glycol 400 in a tissue homogenizer.

We claim as our invention:

1. A method for combatting psychic depression in mammals which comprises administering to a psychically depressed mammal in need of said treatment an effective dosage for combatting the psychic depression of the compound of the formula

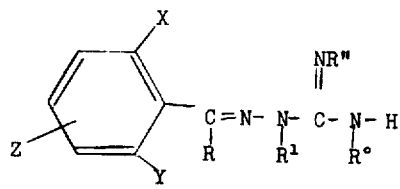

wherein X is halogen or trifluoromethyl, Y and Z may be the same or different and are hydrogen, halogen, trifluoromethyl or alkyl of 1 to 4 carbon atoms, R, R', R" and R° each hydrogen, alkyl of 1 to 4 carbon atoms, alkenyl of 2 to 4 carbon atoms or alkynyl of 2 to 4 carbon atoms with the proviso that R" and R° may together form an alklene or alkenylene bridge of 2 to 4 carbon atoms, with the further proviso that one of Y and R must be hydrogen, or a pharmaceutically acceptable salt thereof.

2. A method according to claim 1 wherein X and Y each is a middle halogen and Z, R, R', R", R° each is hydrogen and the salt is a hydrohalic acid salt.

* * * * *